United States Patent
Pollock et al.

(10) Patent No.: US 11,816,822 B2
(45) Date of Patent: *Nov. 14, 2023

(54) TECHNOLOGIES FOR DETERMINING THE ACCURACY OF THREE-DIMENSIONAL MODELS FOR USE IN AN ORTHOPAEDIC SURGICAL PROCEDURE

(71) Applicant: DePuy Synthes Products, Inc., Raynham, MA (US)

(72) Inventors: Shawnoah S. Pollock, South Bend, IN (US); R. Patrick Courtis, Boston, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/827,991

(22) Filed: May 30, 2022

(65) Prior Publication Data

US 2022/0292663 A1 Sep. 15, 2022

Related U.S. Application Data

(63) Continuation of application No. 16/586,884, filed on Sep. 27, 2019, now Pat. No. 11,348,216.

(51) Int. Cl.
*G06K 9/00* (2022.01)
*G06T 7/00* (2017.01)
(Continued)

(52) U.S. Cl.
CPC .............. *G06T 7/0002* (2013.01); *G06T 7/13* (2017.01); *G06T 7/70* (2017.01); *G06T 15/06* (2013.01);
(Continued)

(58) Field of Classification Search
CPC ........... G06T 7/0002; G06T 7/13; G06T 7/70; G06T 15/06; G06T 2207/10116;
(Continued)

(56) References Cited

U.S. PATENT DOCUMENTS 9,898,825 B2 * 2/2018 Rivet-Sabourin ....... G06T 7/155
11,134,908 B2 10/2021 Pollock et al.
(Continued)

OTHER PUBLICATIONS

Z. Zhu et al., "An automatic 2D-3D image matching method for reproducing spatial knee joint positions using single or dual fluoroscopic images," Computer Methods in Biomechanics and Biomedical Engineering, 2011, 22 pages, vol. 15, No. 11. (Year: 2011).*

(Continued)

*Primary Examiner* — Van D Huynh
(74) *Attorney, Agent, or Firm* — Barnes & Thornburg LLP

(57) ABSTRACT

Technologies for determining the accuracy of three-dimensional models include a device having circuitry to obtain two-dimensional images of an anatomical object (e.g., a bone of a human joint), to obtain a candidate three-dimensional model of the anatomical object, and to produce two-dimensional silhouettes of the candidate three-dimensional model. The circuitry is also to apply an edge detection algorithm to the two-dimensional images to produce corresponding edge images and to compare the two-dimensional silhouettes to the edge images to produce a score indicative of an accuracy of the candidate three-dimensional model.

20 Claims, 10 Drawing Sheets

(51) Int. Cl.
*G06T 7/13* (2017.01)
*G06T 7/70* (2017.01)
*G06T 15/06* (2011.01)

(52) U.S. Cl.
CPC ........... *G06T 2207/10116* (2013.01); *G06T 2207/30008* (2013.01); *G06T 2207/30244* (2013.01)

(58) Field of Classification Search
CPC . G06T 2207/30008; G06T 2207/30244; G06T 2207/30204; G06T 7/75; G06T 7/344; G06T 2207/30052; G06T 2210/41; G06T 2219/2004; A61B 2034/105
USPC ........................................................ 382/173
See application file for complete search history.

(56) References Cited

U.S. PATENT DOCUMENTS

| | | | |
|---|---|---|---|
| 11,348,216 | B2 | 5/2022 | Pollock et al. |
| 2008/0143707 | A1 | 6/2008 | Mitchell |
| 2010/0034484 | A1* | 2/2010 | Kido ............... G06V 10/751 382/294 |
| 2010/0259546 | A1* | 10/2010 | Yomdin ............... G06T 7/12 345/473 |
| 2013/0166256 | A1* | 6/2013 | Wirx-Speetjens ..... B33Y 50/00 703/1 |
| 2015/0228063 | A1* | 8/2015 | Minakawa ............ G06T 7/0002 382/151 |
| 2016/0070973 | A1* | 3/2016 | Rivet-Sabourin ......... G06T 7/12 382/199 |
| 2019/0180466 | A1 | 6/2019 | Tao |
| 2021/0134070 | A1 | 5/2021 | de Almeida Barreto |
| 2021/0169367 | A1 | 6/2021 | Mahfouz |
| 2022/0022831 | A1 | 1/2022 | Pollock et al. |

OTHER PUBLICATIONS

European Patent Office, Search Report and Opinion for related EP20198249.3, dated Feb. 3, 2021, 13 pages.
European Patent Office, Search Report and Opinion for related EP20198250.1, dated Feb. 3, 2021, 12 pages.
Z. Zhu et al., "An automatic 2D-3D image matching method for reproducing spatial knee joint positions using single or dual fluoroscopic images," Computer Methods in Biomechanics and Biomedical Engineering, 2011, 22 pages, vol. 15, No. 11.
P. Markelj et al., "A robust optimization strategy for intensity-based 2D/3D registration of knee implant models to single-plane fluoroscopy," Medical Image Analysis, Apr. 13, 2010, 20 pages, vol. 16, No. 3, Oxford University Press, Oxford, GB.
J. Hermans et al., "A review of 3D/2D registration methods for image-guided interventions," Proceedings of SPIE, Mar. 2007, 13 pages, vol. 6512.

* cited by examiner

TECHNOLOGIES FOR DETERMINING THE ACCURACY OF THREE-DIMENSIONAL MODELS FOR USE IN AN ORTHOPAEDIC SURGICAL PROCEDURE

This application is a continuation of U.S. patent application Ser. No. 16/586,884, filed on Sep. 27, 2019, the entire disclosure of which is incorporated by reference herein.

CROSS-REFERENCE TO RELATED APPLICATIONS

The present application is related to U.S. patent application Ser. No. 16/586,887, filed on Sep. 27, 2019, now U.S. Pat. No. 11,134,908, and U.S. patent application Ser. No. 14/493,003, filed on Oct. 4, 2021, which are both entitled "TECHNOLOGIES FOR DETERMINING THE SPATIAL ORIENTATION OF INPUT IMAGES FOR USE IN AN ORTHOPAEDIC SURGICAL PROCEDURE."

TECHNICAL FIELD

The present disclosure relates to orthopaedic surgical procedures, and, more specifically, to technologies for determining the accuracy of three-dimensional models for use in an orthopaedic surgical procedure.

BACKGROUND

Some three-dimensional modeling systems, such as x-ray based systems, produce a three-dimensional model of an object based on a set of two-dimensional images (e.g., x-ray images) of the object from different viewpoints. To lower the likelihood that the resulting model is inaccurate, for example due to an incorrect orientation in three-dimensional space, a human operator may place calibration markers (e.g., physical objects of known size and/or locations) on or near the object being imaged and modeled. However, such calibration objects are complex and time consuming to position. Furthermore, in such systems, the process of validating the accuracy of a three-dimensional model must be performed by a human operator who visually inspects the model and compares the model to the original object to determine whether the model is properly aligned and sized.

SUMMARY

In one aspect, the present disclosure describes a device having circuitry to obtain two-dimensional images of an anatomical object (e.g., a bone of a human joint), obtain a candidate three-dimensional model of the anatomical object, and produce two-dimensional silhouettes of the candidate three-dimensional model. The circuitry is also to apply an edge detection algorithm to the two-dimensional images to produce corresponding edge images and compare the two-dimensional silhouettes to the edge images to produce a score indicative of an accuracy of the candidate three-dimensional model.

In another aspect, the present disclosure describes one or more machine-readable storage media comprising a plurality of instructions stored thereon that, in response to being executed, cause a device to obtain two-dimensional images of an anatomical object, obtain a candidate three-dimensional model of the anatomical object, and produce two-dimensional silhouettes of the candidate three-dimensional model. The plurality of instructions additionally cause the device to apply an edge detection algorithm to the two-dimensional images to produce corresponding edge images, and compare the two-dimensional silhouettes to the edge images to produce a score indicative of an accuracy of the candidate three-dimensional model.

In yet another aspect, the present disclosure describes a method that includes obtaining, by a device, two-dimensional images of an anatomical object, obtaining, by the device, a candidate three-dimensional model of the anatomical object, and producing, by the device, two-dimensional silhouettes of the candidate three-dimensional model. The method also includes applying, by the device, an edge detection algorithm to the two-dimensional images to produce corresponding edge images and comparing, by the device, the two-dimensional silhouettes to the edge images to produce a score indicative of an accuracy of the candidate three-dimensional model.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
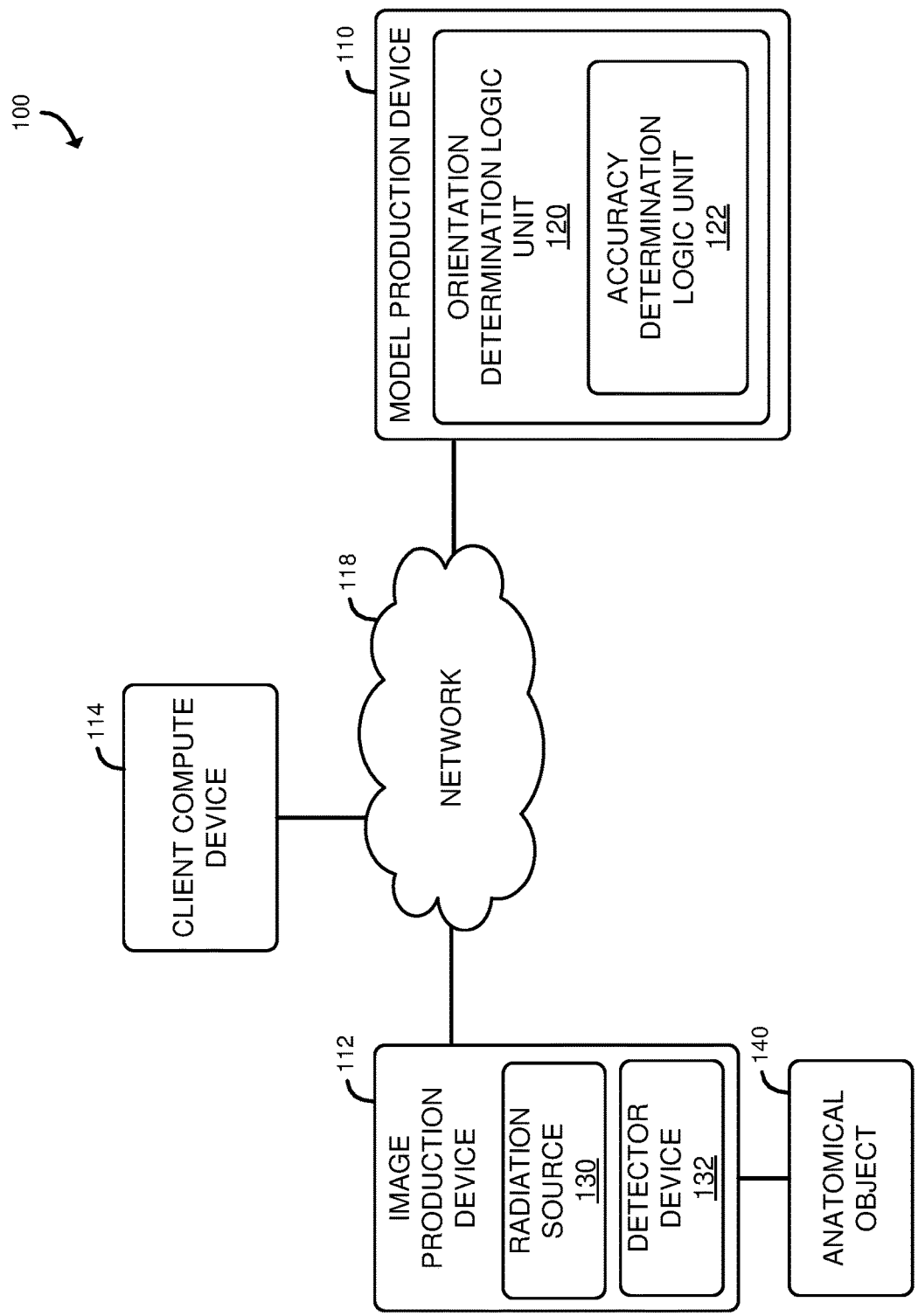
FIG. 1 is a simplified diagram of one embodiment of a system for determining the accuracy of a three-dimensional model produced from two-dimensional images of an object.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a system 100 for determining the accuracy of a three-dimensional model produced from two-dimensional images of an object includes a model production device 110 in communication with an image production device 112 and a client compute device 114 through a network 116. Unlike other systems, the system 100 determines of the accuracy of three-dimensional models without relying on extensive human assistance and complex calibration markers, as described in more detail herein. In the illustrative embodiment, the model production device 110, in operation may obtain a set of two-dimensional images (e.g., x-ray images) of an object, such as an anatomical object 140 (e.g., a portion of a human body, such as one or more bones of a human joint), from multiple different viewpoints (e.g., orthogonal viewpoints). Further, the model production device 110, in the illustrative embodiment, produces a three-dimensional model of the anatomical object 140 from the obtained two-dimensional images. In doing so, the model production device 110 determines the scale of the model based on known dimensions of a reference object (e.g., a steel ball having a diameter of 25 millimeters) in the images and based on candidate values that define a possible orientation of the anatomical object 140 (e.g., rotation and translation). Further, the model production device 110 determines an accuracy of the produced model based on a scoring process in which the model production device 110 compares two-dimensional silhouettes of the three-dimensional model to edge-detected versions of the obtained two-dimensional images, as described in more detail herein. Further, the model production device 110 may iteratively adjust the candidate values (e.g., according to a gradient ascent process, a particle swarm process, a genetic algorithm, machine learning, etc.) to produce further versions of the model until a threshold accuracy score is obtained (e.g., an accuracy score that is greater than or equal to a target accuracy, the highest accuracy score out of a set of a predefined number of produced accuracy scores, an accuracy score indicative of a local maximum, etc.).

In the illustrative embodiment, the model production device 110 includes an orientation determination logic unit 120, which may be embodied as software or any device or circuitry (e.g., a co-processor, reconfigurable circuitry, an application specific integrated circuit (ASIC), a field programmable gate array (FPGA), etc.) configured to perform the model production and accuracy scoring operations described above (e.g., offloading those operations from a general purpose processor of the model production device 110). Further, in the illustrative embodiment, the orientation determination logic unit 120 includes an accuracy determination logic unit 122, which may be embodied as software or any device or circuitry (e.g., a co-processor, reconfigurable circuitry, an application specific integrated circuit (ASIC), a field programmable gate array (FPGA), etc.) configured to perform the operations that constitute the accuracy scoring process (e.g., producing three-dimensional silhouettes of a model, projecting the three-dimensional silhouettes onto imaging surfaces to produce two-dimensional silhouettes, applying edge detection operations to obtained two-dimensional images of the anatomical object 140 to produce edge images (e.g., edge-detected versions of the two-dimensional images), and comparing edges in the two-dimensional silhouettes to the edges in the edge images to determine a score indicative of an accuracy of the model).

The image production device 112, in the illustrative embodiment, may be embodied as any device (e.g., a computer, a compute device, etc.) capable of producing a set of two-dimensional images of an object (e.g., the anatomical object 140) from multiple different viewpoints (e.g., angles). In the illustrative embodiment, the image production device 112 includes one or more a radiation sources (e.g., x-ray sources), each of which may be embodied as any device capable of directing radiation (e.g., x-ray radiation) at an object. The image production device 112 also includes one or more detector devices 132, each of which may be embodied as any device capable of producing, from the interaction of the radiation with the anatomical object 140, a corresponding image of the anatomical object 140. As described above, the image production device 112, in the illustrative embodiment, produces two-dimensional images of the anatomical object 140 from multiple different viewpoints (e.g., angles), either by utilizing multiple stationary radiation sources 130 and detector devices 132 arranged in different orientations with respect to the anatomical object 140 and/or by iteratively producing images of the anatomical object 140 from different viewpoints using one or more movable radiation sources 130 and detector devices 132.

Additionally the system 100 may include a client compute device 114 which may be embodied as any device (e.g., a computer, a compute device, etc.) capable of communicating with the image production device 112 and/or the model production device 110 to send requests to (e.g., to produce two-dimensional images of an anatomical object, to produce a model from the images, to determine an accuracy score of the model, etc.) and receive data from (e.g., the produced two-dimensional images, the produced model, one or more accuracy scores, etc.) one or more of the device(s) 110, 112.

Figure 2:
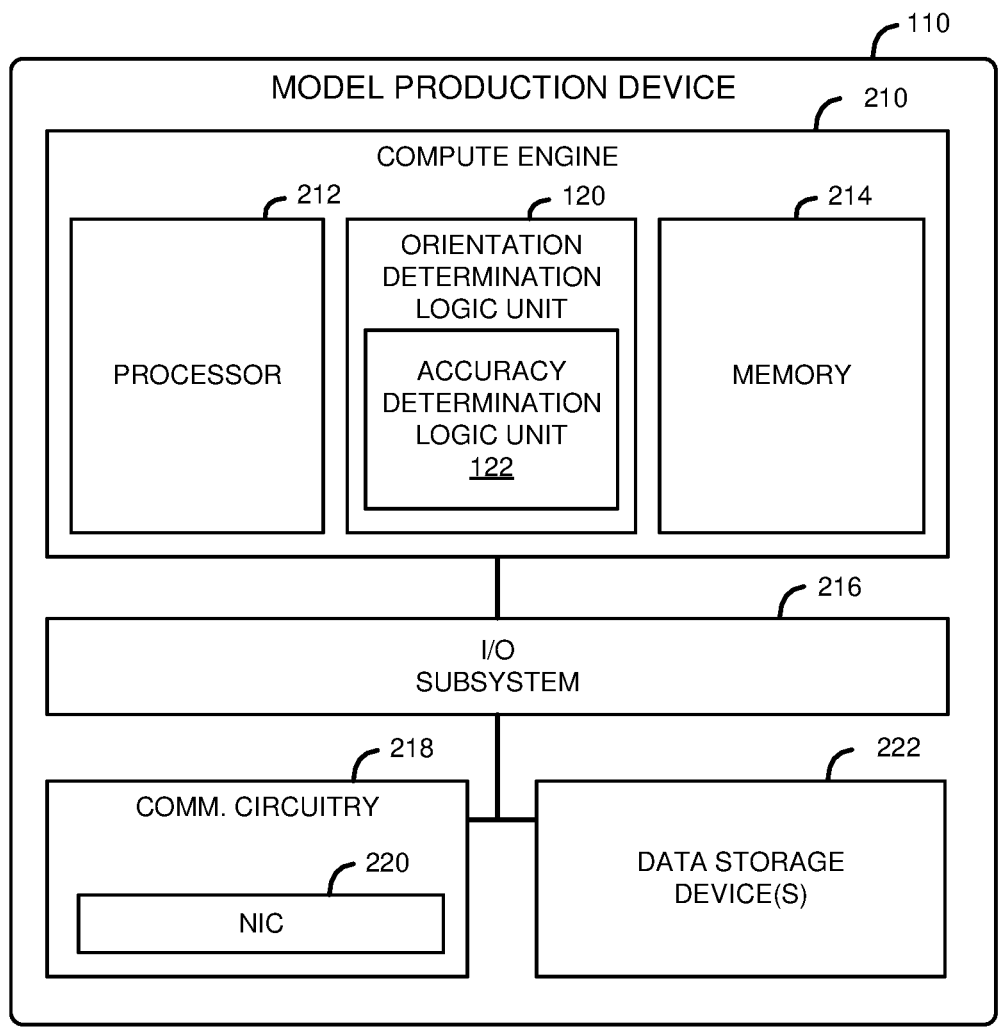
FIG. 2 is a simplified block diagram of one embodiment of a model production device that may be included in the system of FIG. 1.

Referring now to FIG. 2, the illustrative model production device 110 may be embodied as a compute device (e.g., a computer) that includes a compute engine (also referred to herein as "compute engine circuitry") 210, an input/output (I/O) subsystem 216, communication circuitry 218, and one or more data storage devices 222. Of course, in other embodiments, the model production device 110 may include other or additional components, such as those commonly found in a computer (e.g., a display, peripheral devices, etc.). Additionally, in some embodiments, one or more of the illustrative components may be incorporated in, or otherwise form a portion of, another component. The compute engine 210 may be embodied as any type of device or collection of devices capable of performing various compute functions described below. In some embodiments, the compute engine 210 may be embodied as a single device such as an integrated circuit, an embedded system, a field-programmable gate array (FPGA), a system-on-a-chip (SOC), or other integrated system or device. In the illustrative embodiment, the compute engine 210 includes or is embodied as a processor 212, a memory 214, the orientation determination logic unit 120, and the accuracy determination logic unit 122, described above with reference to FIG. 1. The processor 212 may be embodied as any type of processor capable of performing the functions described herein. For example, the processor 212 may be embodied as a multi-core processor(s), a microcontroller, or other processor or processing/controlling circuit. In some embodiments, the processor 212 may be embodied as, include, or be coupled to an FPGA, an application specific integrated circuit (ASIC), reconfigurable hardware or hardware circuitry, or other specialized hardware to facilitate performance of the functions described herein.

The main memory 214 may be embodied as any type of volatile (e.g., dynamic random access memory (DRAM), etc.) or non-volatile memory or data storage capable of performing the functions described herein. Volatile memory may be a storage medium that requires power to maintain the state of data stored by the medium. In some embodiments, all or a portion of the main memory 214 may be integrated into the processor 212. In operation, the main memory 214 may store various software and data used during operation such as one or more applications, data operated on by the application(s) (e.g., two-dimensional images, three-dimensional models, candidate values for orientation, silhouettes, edge images, accuracy scores, etc.), libraries, and drivers.

The compute engine 210 is communicatively coupled to other components of the model production device 110 via the I/O subsystem 216, which may be embodied as circuitry and/or components to facilitate input/output operations with the compute engine 210 (e.g., with the processor 212 and/or the main memory 214) and other components of the model production device 110. For example, the I/O subsystem 216 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some embodiments, the I/O subsystem 216 may form a portion of a system-on-a-chip (SoC) and be incorporated, along with one or more of the processor 212, the main memory 214, and other components of the model production device 110, into the compute engine 210.

The communication circuitry 218 may be embodied as any communication circuit, device, or collection thereof, capable of enabling communications over a network between the model production device 110 and another compute device (e.g., the image production device 112, the client compute device 114, etc.). The communication circuitry 218 may be configured to use any one or more communication technology (e.g., wired or wireless communications) and associated protocols (e.g., Ethernet, Wi-Fi®, WiMAX, Bluetooth®, cellular, etc.) to effect such communication.

The illustrative communication circuitry 218 includes a network interface controller (NIC) 220. The NIC 220 may be embodied as one or more add-in-boards, daughter cards, network interface cards, controller chips, chipsets, or other devices that may be used by the model production device 110 to connect with another compute device (e.g., the image production device 112, the client compute device 114, etc.). In some embodiments, the NIC 220 may be embodied as part of a system-on-a-chip (SoC) that includes one or more processors, or included on a multichip package that also contains one or more processors. In some embodiments, the NIC 220 may include a local processor (not shown) and/or a local memory (not shown) that are both local to the NIC 220. In such embodiments, the local processor of the NIC 220 may be capable of performing one or more of the functions of the compute engine 210 described herein. Additionally or alternatively, in such embodiments, the local memory of the NIC 220 may be integrated into one or more components of the model production device 110 at the board level, socket level, chip level, and/or other levels.

The one or more illustrative data storage devices 222 may be embodied as any type of devices configured for short-term or long-term storage of data such as, for example, memory devices and circuits, memory cards, hard disk drives, solid-state drives, or other data storage devices. Each data storage device 222 may include a system partition that stores data and firmware code for the data storage device 222. Each data storage device 222 may also include one or more operating system partitions that store data files and executables for operating systems.

The image production device 112 and the client compute device 114 may have components similar to those described in FIG. 2 with reference to the model production device 110. The description of those components of the model production device 110 is equally applicable to the description of components of the image production device 112 and the client compute device 114, with the exception that, in some embodiments, the orientation determination logic unit 120 and the accuracy determination logic unit 122 are not included in devices other than the model production device 110. Further, it should be appreciated that any of the model production device 110, the image production device 112, and the client compute device 114 may include other components, sub-components, and devices commonly found in a computing device, which are not discussed above in reference to the model production device 110 and not discussed herein for clarity of the description. Further, it should be understood that one or more components of a compute device may be distributed across any distance, and are not necessarily housed in the same physical unit.

Referring back to FIG. 1, the model production device 110, the image production device 112, and the client compute device 114 are illustratively in communication via a network 116, which may be embodied as any type of data communication network, including a global network (e.g., the internet), a one or more wide area network (WANs), local area networks (LANs) digital subscriber line (DSL) networks, cable networks (e.g., coaxial networks, fiber networks, etc.), cellular networks (e.g., Global System for Mobile Communications (GSM), 3G, Long Term Evolution (LTE), Worldwide Interoperability for Microwave Access (WiMAX), etc.), radio access networks (RANs), or any combination thereof. Further, while shown as separate devices in FIG. 1, it should be understood that in some embodiments, one or more of the model production device 110, the image production device 112, and the client compute device 114 may be combined into a single unit.

Figure 3:
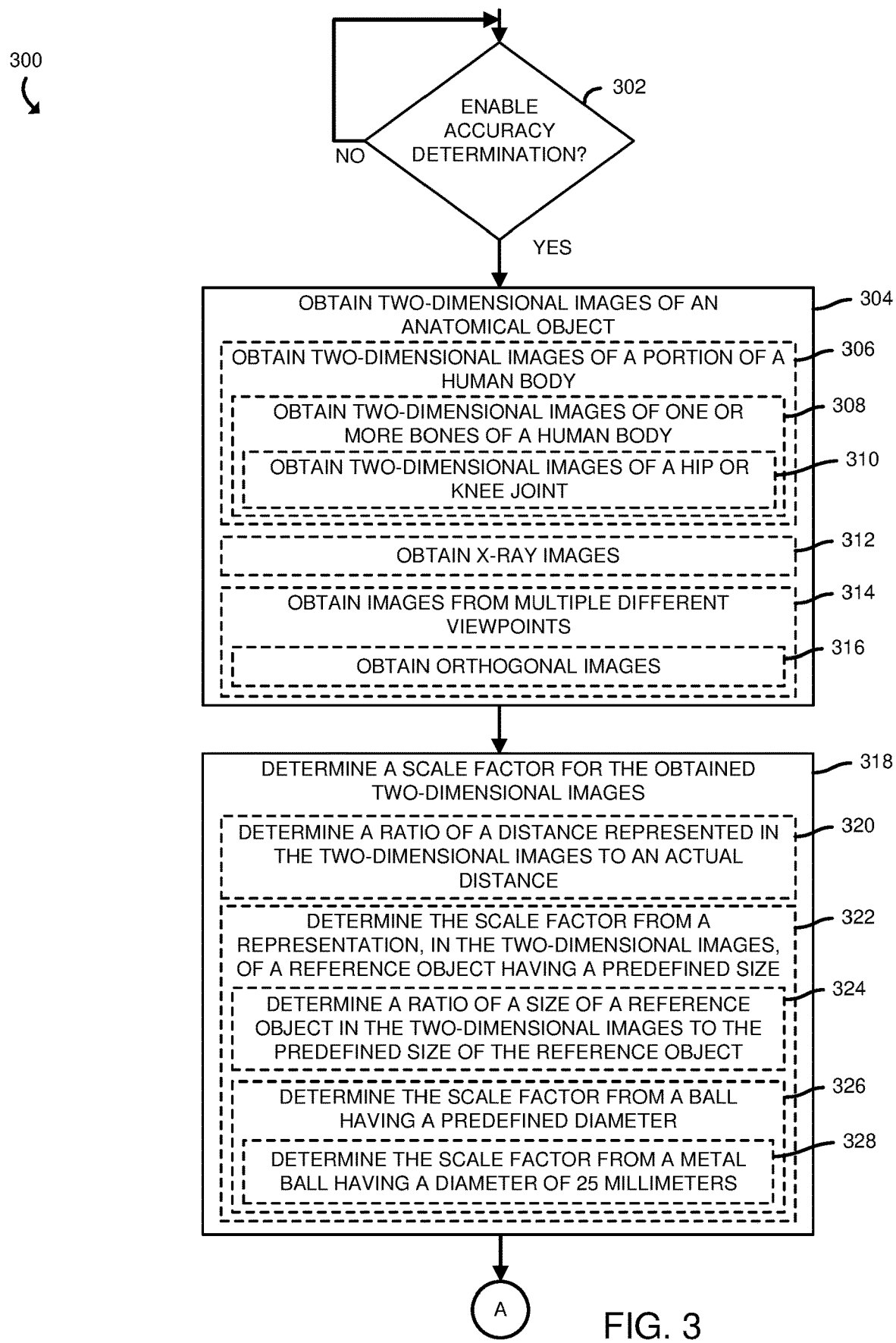
FIGS. 3-8 are simplified block diagrams of one embodiment of a method that may be performed by the model production device of FIGS. 1 and 2 for determining the accuracy of a three-dimensional model produced from two-dimensional images of an object.

Referring now to FIG. 3, the model production device 110, in operation, may execute a method 300 for determining the accuracy of a three-dimensional model produced from two-dimensional images of an object (e.g., the anatomical object 140). The method 300 begins with block 302, in which the model production device 110 determines whether to enable accuracy determination. The model production device 110 may determine to enable accuracy determination in response to a determination that the model production device 110 is equipped with the orientation determination logic unit 120 and the accuracy determination logic unit 122, in response to a determination that a configuration setting (e.g., in the memory 214) indicates to enable accuracy determination, in response to a request from another device (e.g., the client compute device 114) to enable accuracy determination, and/or based on other factors. In response to a determination to enable accuracy determination, the method 300 advances to block 304, in which the model production device 110 obtains two-dimensional images of an anatomical object (e.g., from the image production device 112). In doing so, in the illustrative embodiment, the model production device 110 obtains two-dimensional images of a portion of a human body, as indicated in block 306. As indicated in block 308, the model production device 110 may obtain two-dimensional images of one or more bones of a human body. For example, and as indicated in block 310, the model production device 110 may obtain two-dimensional images of a hip or a knee joint. In the illustrative embodiment, in obtaining the two-dimensional images, the model production device 110 obtains x-ray images (e.g., images produced by passing x-ray radiation (e.g., from the radiation source 130) through a patient's body onto a detector (e.g., the detector device 132)), as indicated in block 312. In other embodiments, the two-dimensional images may be formed from other types of electromagnetic radiation (e.g., visible light, infrared light, etc.). The model production device 110, in the illustrative embodiment, obtains two-dimensional images of the anatomical object 140 from multiple different viewpoints (e.g., angles), as indicated in block 314. In doing so, in the illustrative embodiment, the model production device 110 obtains orthogonal images (e.g., images from viewpoints that are perpendicular to each other), as indicated in block 316. In other embodiments, the viewpoints maybe at other angles relative to each other.

Subsequently, in block 318, the model production device 110 determines a scale factor (e.g., data indicative of an amount by which the sizes of objects as represented in the two-dimensional images differ from their actual size) for the obtained two-dimensional images. In doing so, and as indicated in block 320, the model production device 110 determines a ratio of a distance (e.g., a diameter, a length, etc. of an object) represented in the two-dimensional images to an actual distance (e.g., the actual diameter, length, etc. of the object). As an example, and as indicated in block 322, the model production device 110 may determine the scale factor from a representation, in the two-dimensional images, of a reference object having a predefined (e.g., known) size. In the illustrative embodiment, the model production device 110 may determine a ratio of the size of the reference object as it appears in the obtained two-dimensional images to the predefined size of that reference object, as indicated in block 324. As indicated in block 326, the model production device 110 may determine the scale factor from a ball having a predefined diameter. In the illustrative embodiment, and as indicated in block 328, the model production device 110 may determine the scale factor from a metal ball having a predefined diameter of 25 millimeters (e.g., by determining the ratio of the diameter of the ball as represented in the two-dimensional images to the known diameter of 25 millimeters). That is, the metal ball may be physically present with (e.g., next to, attached to, etc.) the patient and is imaged by the image production device 112. Subsequently, the method 300 advances to block 330 of FIG. 4, in which the model production device 110 determines candidate values indicative of translation and rotation of the anatomical object 140 represented in the obtained two-dimensional images.

Figure 4:
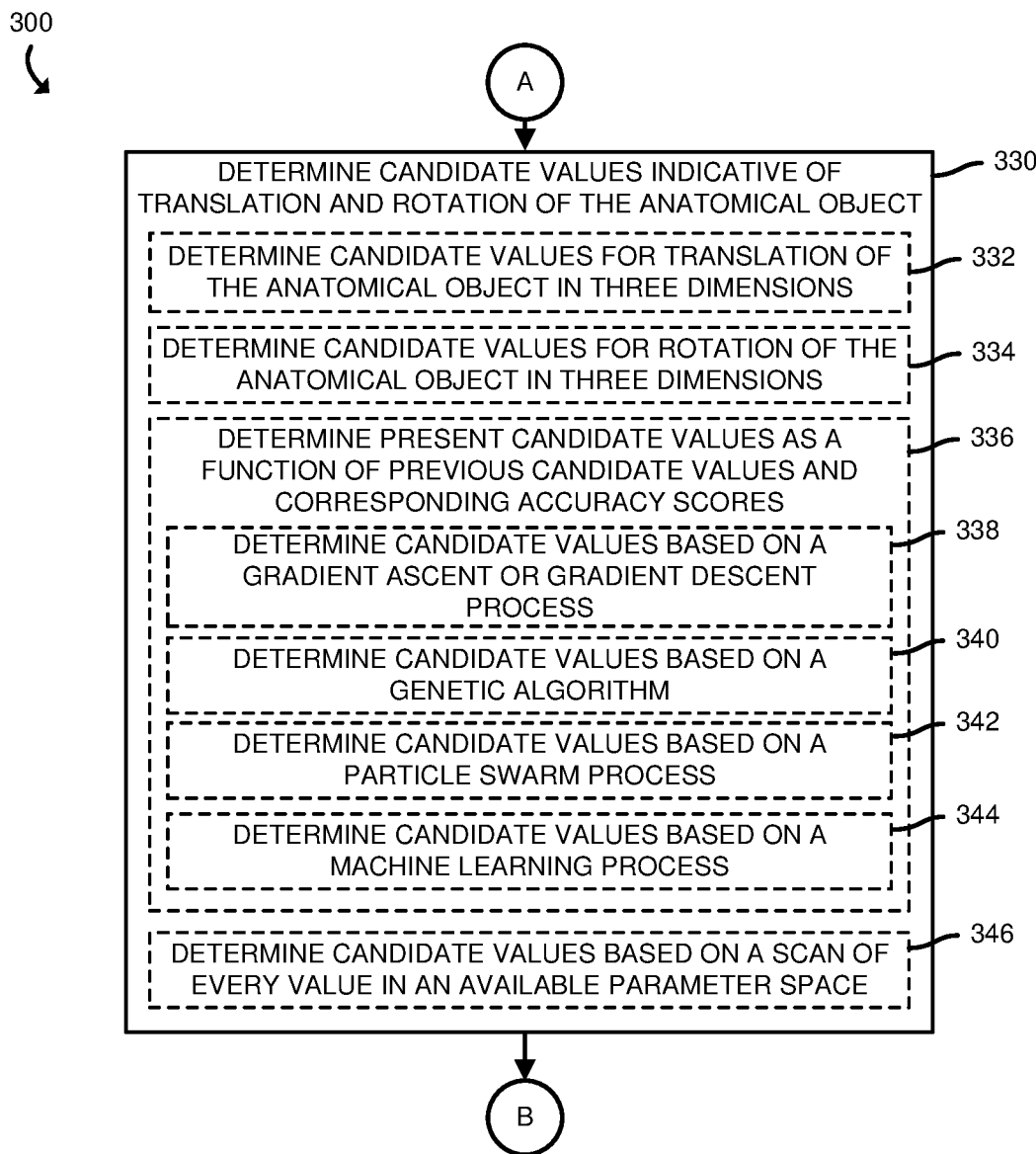

Referring now to FIG. 4, in determining the candidate values, the model production device 110, determines candidate values for the translation of the anatomical object in three dimensions (e.g., along an x-axis, a y-axis, and a z-axis), as indicated in block 332. Similarly, and as indicated in block 332, the model production device 110, in the illustrative embodiment, determines candidate values for rotation of the anatomical object 140 in three dimensions (e.g., along the x-axis, the y-axis, and the z-axis), as indicated in block 334. The candidate values may be determined in a variety of ways, depending on the embodiment. For example, and as indicated in block 336, the model production device 110 may determine the present candidate values as a function of (e.g., based on) previous candidate values and corresponding accuracy scores of models produced using those values (e.g., from previous iterations of the method 300). As indicated in block 338, the model production device 110 may determine candidate values based on a gradient ascent process (e.g., a first-order iterative optimization process for finding the maximum of a function by taking steps proportional to the positive of the gradient, or approximate gradient, of the function at the current point) or a gradient descent process (e.g., to find the minimum of a function). In some embodiments, the model production device 110 may determine the candidate values based on a genetic algorithm (e.g., a metaheuristic that utilizes biologically-based operators such as mutation, crossover, and selection to simulate a process of natural selection to find an optimal solution to a problem), as indicated in block 340.

Additionally or alternatively, the model production device 110 may determine the candidate values based on a particle swarm process (e.g., a process that optimizes a problem by iteratively improving a candidate solution with regard to a given measure of quality (e.g., an accuracy score) by utilizing a population of candidate solutions (referred to as "particles") and moving the particles around in a search-space according to mathematical operations that affect each particle's position and velocity), as indicated in block 342. In some embodiments, the model production device 110 may utilize a machine learning process (e.g., a process that utilizes training data to identify patterns indicative of a mathematical relationship between input variables and outputs) to determine the present candidate values, as indicated in block 344. In other embodiments, the model production device 110 may determine the candidate values based on a scan of every value in an available parameter space (e.g., iteratively trying every possible degree of rotation around each axis, etc.), as indicated in block 346. Subsequently, the method 300 advances to block 348 of FIG. 5 in which the model production device 110 obtains (e.g., produces) a candidate three-dimensional model of the anatomical object 140 as a function of the obtained two-dimensional images (e.g., from block 304), the scale factor (e.g., from block 318), and the candidate values (e.g., from block 330).

Figure 5:
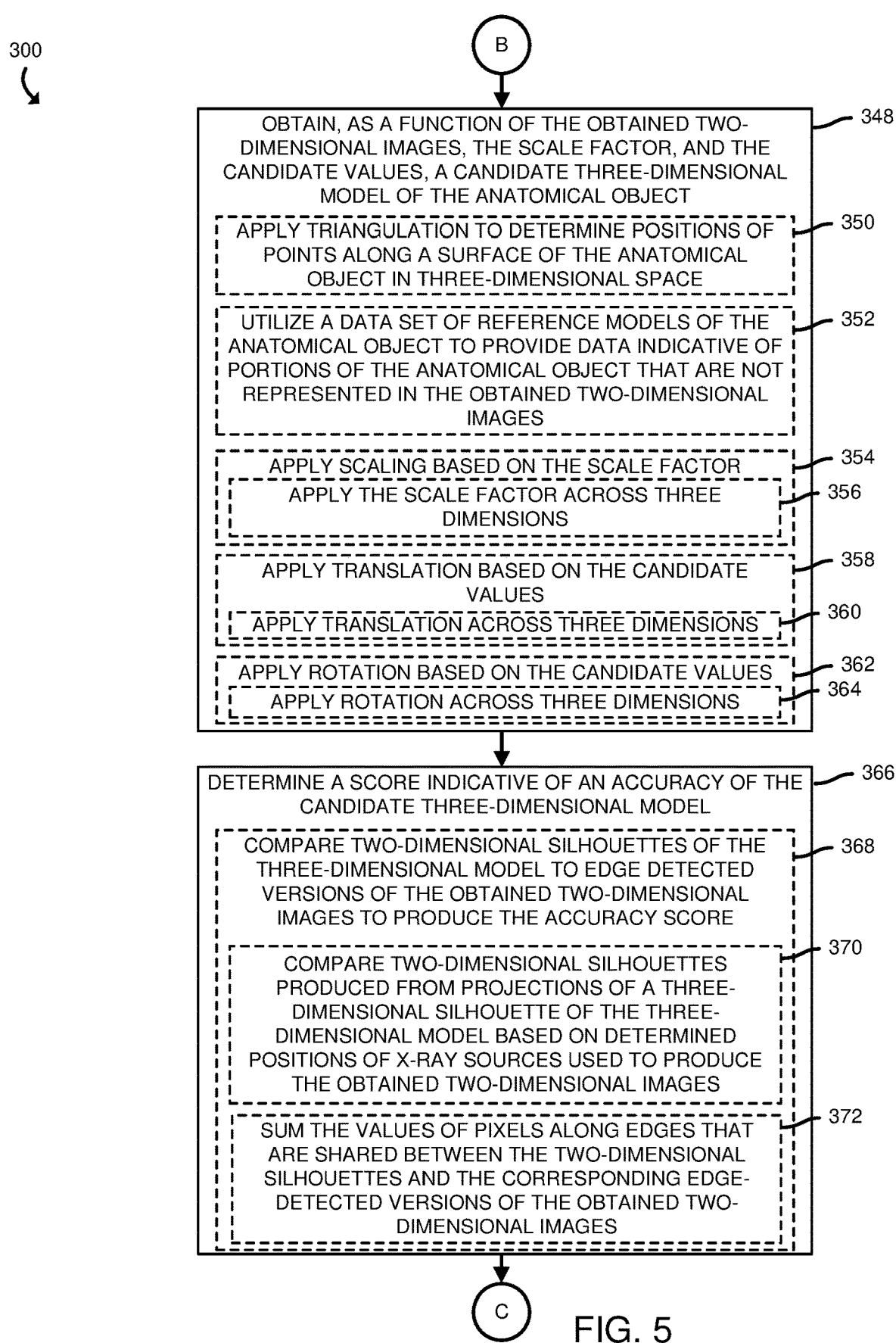

Referring now to FIG. 5, in obtaining the model, and as indicated in block 350, the model production device 110 applies triangulation (e.g., between the anatomical object 140 and the viewpoints from which the two-dimensional images were produced) to determine positions of points along a surface of the anatomical object in three-dimensional space (e.g., each point having an x, y, and z coordinate). As indicated in block 352, the model production device 110 may utilize a data set (e.g., in the memory 214 or in the data storage device 222) of reference models of the anatomical object to provide data indicative of portions of the anatomical object that are not represented in the obtained two-dimensional images (e.g., a portion of a bone is not shown in the obtained two-dimensional images). In the illustrative embodiment, the model production device 110 applies scaling to (e.g., sets the size of) the model based on the scale factor, as indicated in block 354. In doing so, in the illustrative embodiment, the model production device 110 applies the scale factor across three spatial dimensions (e.g., uses the same scale factor to set the size of the model along the x axis, the y axis, and the z axis), as indicated in block 356. The model production device 110 may also apply translation to the model (e.g., change the position of the model) based on the candidate values (e.g., the candidate values for translation, determined in block 332), as indicated in block 358. In doing so, in the illustrative embodiment, the model production device 110 applies translation in three dimensions (e.g., in the x dimension, the y dimension, and the z dimension), as indicated in block 360. Similarly, and as indicated in block 362, the model production device 110 may apply rotation based on the candidate values. In doing so, and as indicated in block 364, the model production device 110 may apply rotation across three dimensions (e.g., rotate the object around an x axis, a y axis, and a z axis by amounts defined in the candidate values).

Subsequently, and as indicated in block 366, the model production device 110 determines a score indicative of an accuracy of the produced three-dimensional model (e.g., the model produced in block 348). In doing so, in the illustrative embodiment, the model production device 110 compares two-dimensional silhouettes of the three-dimensional model to edge-detected versions of the obtained two-dimensional images (e.g., versions of the two-dimensional images in which the edges are indicated in the pixel values (e.g., with a non-zero pixel value) while areas that do not represent edges are represented with different pixel values (e.g., a pixel value of zero)), as indicated in block 368. In doing so, and as indicated in block 370, the model production device 110 compares two-dimensional silhouettes produced from projections of a three-dimensional silhouette of the three-dimensional model (e.g., the model produced in block 348) based on (e.g., projected from) the determined positions of x-ray sources (e.g., the radiation sources 130) used to produce the obtained two-dimensional images. As indicated in block 372, the model production device 110 may sum the values of pixels along edges that are shared between the two-dimensional silhouettes (e.g., from block 370) and the corresponding edge-detected versions of the obtained two-dimensional images, defining the score as the resulting sum.

Figure 6:
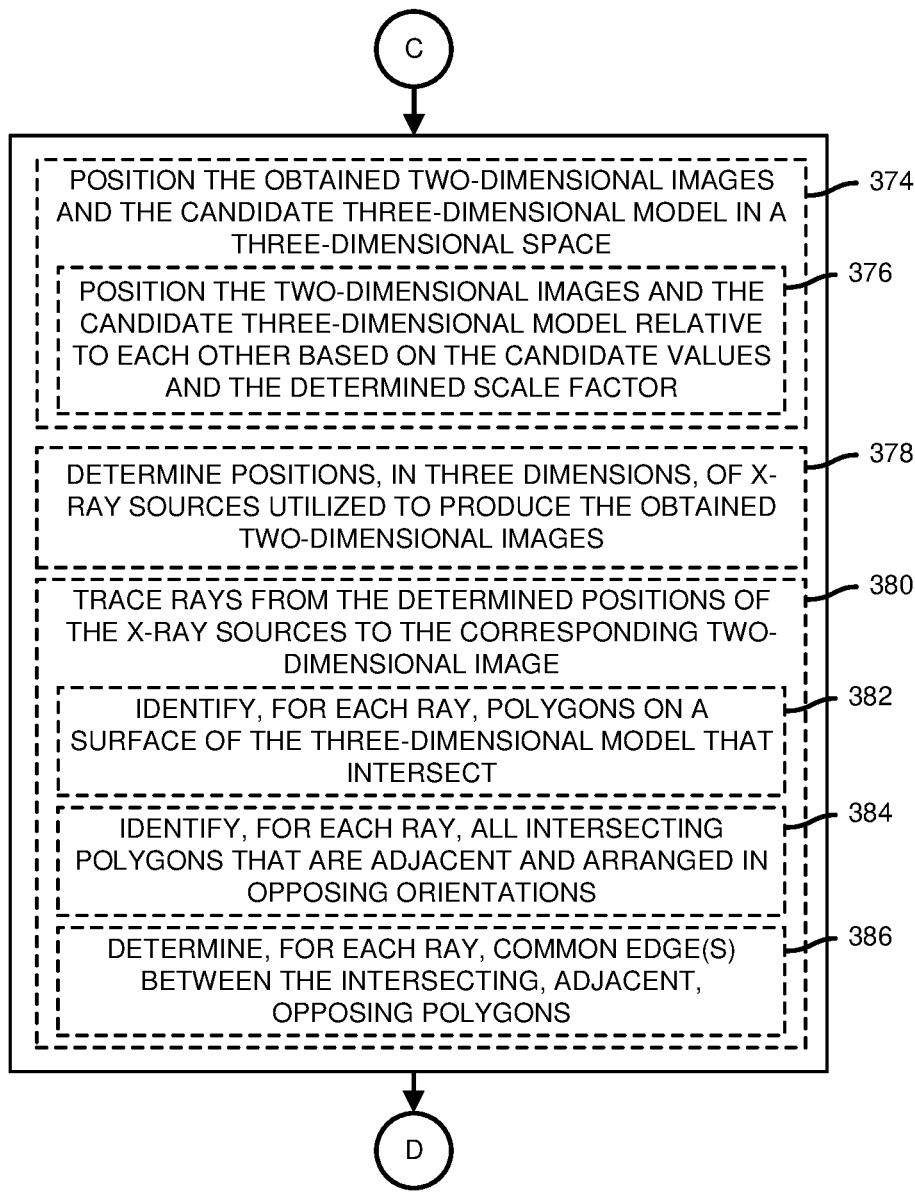

Referring now to FIG. 6, in producing the score indicative of the accuracy of the candidate three-dimensional model, the model production device 110 may position the obtained two-dimensional images and the candidate three-dimensional model in a three-dimensional space, as indicated in block 374. In doing so, and as indicated in block 376, the model production device 110, in the illustrative embodiment, positions the obtained two-dimensional images and the candidate three-dimensional model relative to each other based on the candidate values (e.g., the candidate values from block 330) and the determined scale factor (e.g., from block 318). Additionally, in block 378, the model production device 110, in the illustrative embodiment, determines positions, in three dimensions, of x-ray sources that were utilized to produce the obtained two-dimensional images (e.g., the radiation sources 130). In block 380, the model production device 110 traces rays (e.g., performs raytracing) from the determined position of each x-ray source to the corresponding two-dimensional image. In doing so, the model production device 110 identifies, for each ray, polygons (e.g., triangles) on a surface of the candidate three-dimensional model that intersect, as indicated in block 382. Additionally, and as indicated in block 384, the model production device 110 identifies, for each ray, the intersecting polygons (e.g., from the set of intersecting polygons identified in block 382) that are adjacent to each other and that are arranged in opposing orientations (e.g., pointing in opposite directions). Further, and as indicated in block 386, the model production device 110, in the illustrative embodiment, determines, for each ray, one or more common edges between the intersecting, adjacent, opposing polygons (e.g., the polygons identified in block 384). Subsequently, the method 300 advances to block 388 of FIG. 7, in which the model production device 110 produces, from the one or more common edges (e.g., the edges determined in block 386), three-dimensional silhouettes (e.g., curves defining an outer surface of the candidate three-dimensional model).

Figure 7:
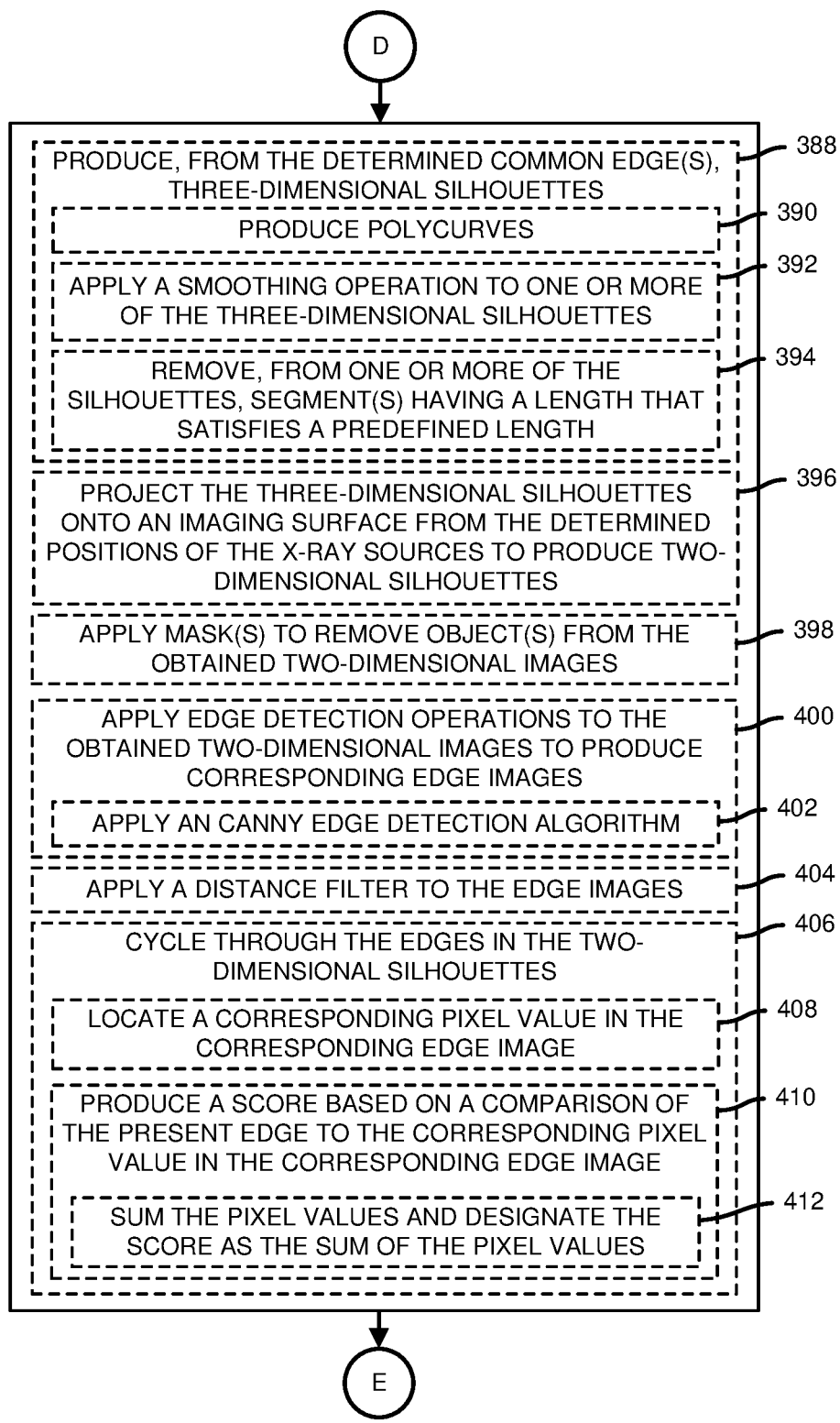

Referring now to FIG. 7, in producing the three-dimensional silhouettes, the model production device 110, in the illustrative embodiment, produces the three-dimensional silhouettes as polycurves (e.g., multiple curves joined together), as indicated in block 390. As indicated in block 392, the model production device 110 may apply a smoothing operation to one or more of the three-dimensional silhouettes and, as indicated in block 394, the model production device 110 may remove, from one or more of the silhouettes, any segments having a length that satisfies a predefined length (e.g., remove any segments that are shorter than a predefined length). Additionally, and as indicated in block 396, the model production device 110 produces two-dimensional silhouettes by projecting the three-dimensional silhouettes (e.g., from block 388) onto one or more imaging surfaces (e.g., planes located where the obtained two-dimensional images were positioned in the three-dimensional space in block 374) from the positions of the x-ray sources (e.g., from the positions of the x-ray sources determined in block 378). The model production device 110 may also apply one or more masks to the obtained two-dimensional images to remove one or more objects (e.g., the reference object from block 322) from the obtained two-dimensional images, as indicated in block 398. Further, in the illustrative embodiment, as indicated in block 400, the model production device 110 applies edge detection operations to the obtained two-dimensional images to produce corresponding edge images (e.g., edge-detected versions of the obtained two-dimensional images). In doing so, and as indicated in block 402, the model production device 110 applies a Canny edge detection algorithm to the obtained two-dimensional images (e.g., applying a Gaussian filter to smooth the image and remove noise, locating intensity gradients in the image, applying non-maximum suppression to eliminate spurious responses to edge detection, applying a double threshold to determine potential edges, and tracking edges with hysteresis). As indicated in block 404 the model production device 110 may additionally apply a distance filter to the edge images. In block 406, in the illustrative embodiment, the model production device 110 cycles through the edges present in the two-dimensional silhouettes (e.g., from block 396). In doing so, the model production device 110 locates the pixels in the edge images that correspond to the present edge from the silhouette, and determines the values of those corresponding pixels, as indicated in block 408. Further, and as indicated in block 410, the model production device 110 produces a score based on a comparison of the edge from the silhouette to the corresponding pixel values in the corresponding edge image. In doing so, and as indicated in block 412, the model production device 110 may sum (e.g., determine a running total of) the pixel values and designate the score as the sum.

Figure 8:
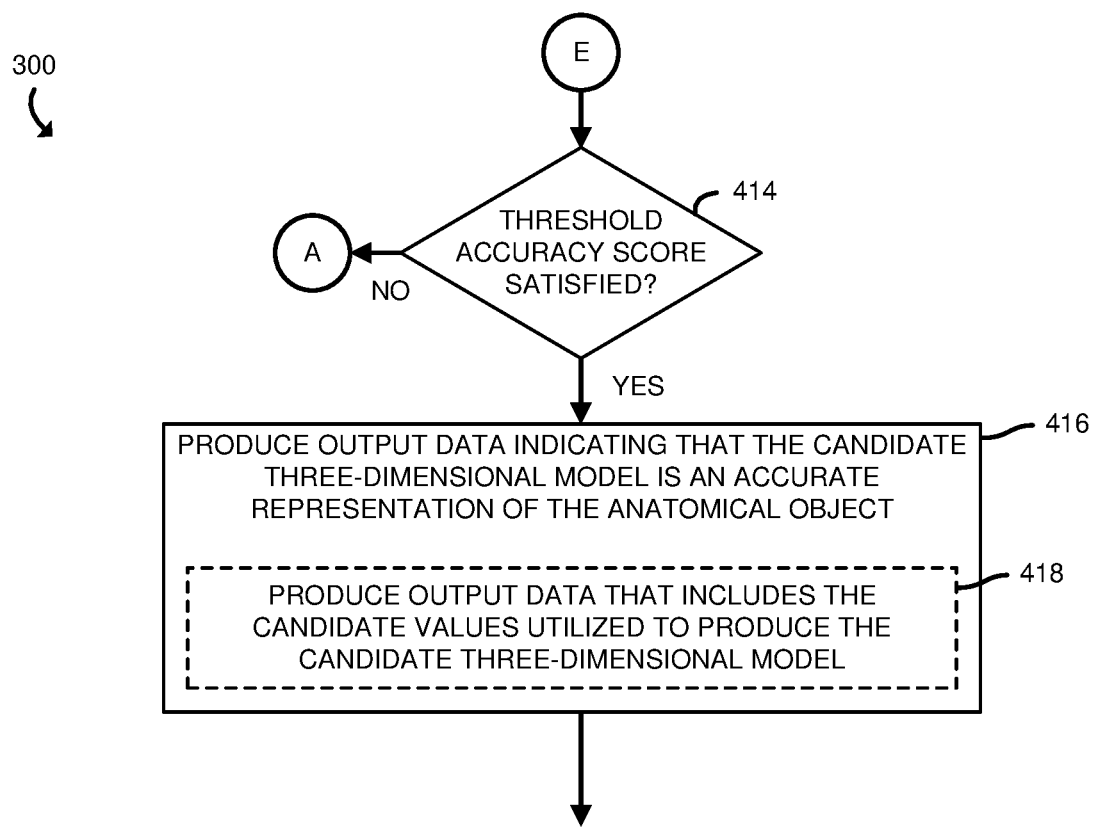
Figure 9:
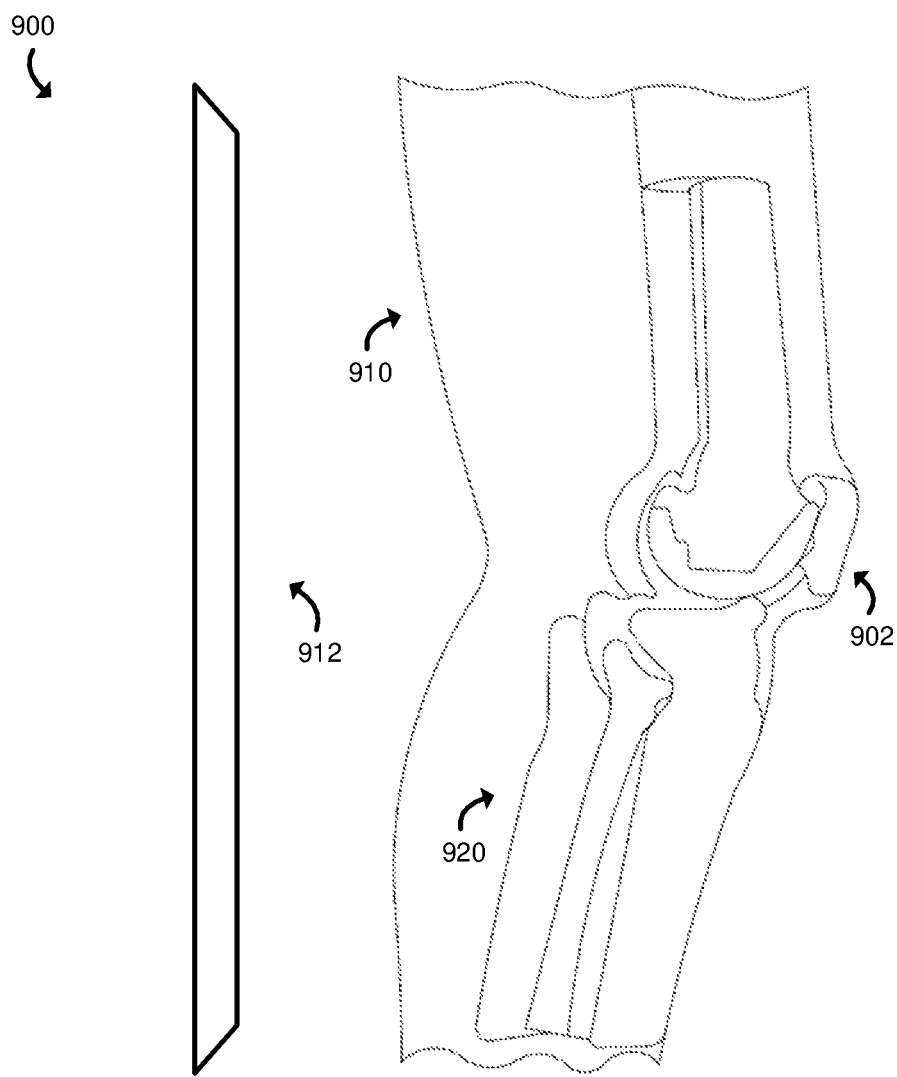
FIG. 9 is a diagram of a spatial orientation of a three-dimensional model of a knee joint, input two-dimensional imagery, and silhouettes that may be generated by the system of FIG. 1.
Figure 10:
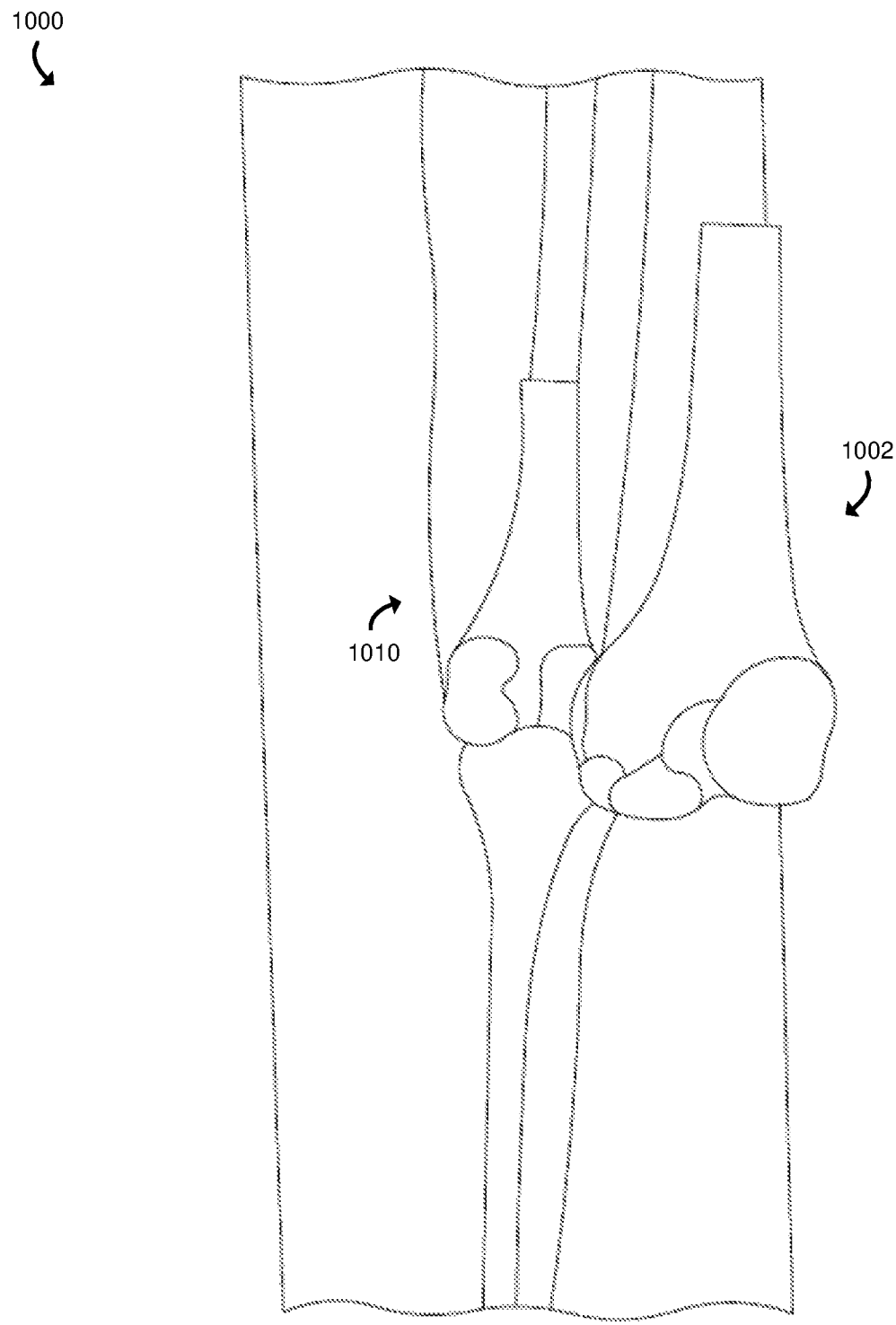
FIG. 10 is a diagram of an alignment of a three-dimensional model of a femur and the alignment of the model to a two-dimensional image of the femur that may be processed by the system of FIG. 1.

Illustrative examples of a spatial orientation 900 of a candidate three-dimensional model 902 (e.g., the candidate model produced in block 348) of a knee joint (e.g., the anatomical object 140), input two-dimensional images 910, 912 (e.g., the two-dimensional images obtained in block 304), and silhouettes 920 (e.g., the silhouettes used in the determination of the score indicative of the accuracy of the candidate model in block 368) are shown in FIG. 9. Illustrative examples of a prototype alignment 1000 (e.g., a spatial orientation) of a candidate three-dimensional model of a femur 1002 to an x-ray image 1010 (e.g., an obtained two-dimensional image from block 304) are shown in FIG. 10. After the model production device 110 has determined the score indicative of the accuracy of the candidate three-dimensional model, the method 300 advances to block 414 of FIG. 8 in which the model production device 110 determines a subsequent course of action based on whether a threshold accuracy score has been satisfied (e.g., by the score determined in block 366).

Referring now to FIG. 8, in determining whether the threshold accuracy score has been satisfied, the model production device 110 may determine whether the score determined in block 366 is equal to or greater than a predefined score, whether the score determined in block 366 is the highest score of a set of scores produced in a series of iterations of the method 300, and/or based on other factors. Regardless, in response to a determination that the threshold accuracy score has not been satisfied, the method 300 loops back to block 330 of FIG. 4, in which the model production device 110 determines a subsequent set (e.g., a different set) of candidate values and produces a subsequent three-dimensional model having a different spatial orientation based on the subsequent set of candidate values. Otherwise (e.g., if the threshold accuracy score has been satisfied), the method 300 advances to block 416 in which the model production device 110 produces output data (e.g., to be displayed, written to memory, and/or sent to another compute device, such as the client compute device 114) indicating that the candidate three-dimensional model is an accurate representation of the anatomical object 140. In doing so, and as indicated in block 418, the model production device 110 may produce output data that includes the candidate values that were utilized to produce the candidate three-dimensional model. The output data may also include the scale factor used in producing the candidate three-dimensional model.

As an illustrative example of the method 300, the model production device 110 may obtain, from the image production device, a set of two-dimensional X-ray images of a patient's knee joint. In the images, a metal ball is present. The model production device 110 is configured to detect the presence of the metal ball, which has a known (e.g., to the model production device 110) diameter of 25 millimeters. In the example, the metal ball is 100 pixels wide in a two-dimensional X-ray image obtained by the model production device 110. As such, the model production device 110 determines that every four pixels represents 1 millimeter (e.g., a 4 to 1 scaling factor). Given that the metal ball is symmetrical, the model production device 110 may fix the scaling factor across the x, y, and z dimensions (e.g., 4 pixels in any direction represents 1 millimeter in that direction).

Next, in the illustrative example, the model production device 110 determines candidate values for translation and rotation of the bones of the knee joint in the X-ray images. In doing so, the model production device 110 selects a possible translation of twenty millimeters along the x axis, the y axis, and the z axis. Additionally, the model production device 110 selects a possible translation of twenty degrees clockwise along each of the x axis, the y axis, and the z axis. The model production device 110 then obtains a candidate three-dimensional model of the bones of the knee joint from the X-ray images using any known 2D/3D conversion method (e.g., TruMatch® 2D3D), filling in missing bone details using reference models of bones of human knee joints. In the process, the model production device 110 applies a translation of twenty millimeters along each of the x axis, the y axis, and the z axis (e.g., an assumption that the patient moved twenty millimeters in each dimension from a position that the reference knee joint models are based on), and a rotation of twenty degrees clockwise along the x axis, the y axis, and the z axis (e.g., an assumption that the X-ray detector that produced the X-ray images was rotated by twenty degrees clockwise, or that the patient rotated (e.g., due to flexion of the knee joint) one or more bones of the knee joint by twenty degrees clockwise, along each axis relative to an orientation that the reference knee joint models are based on), and scales the model using the scaling factor of 4 pixels for every one millimeter. The model production device 110 then determines the accuracy of the resulting model by comparing two-dimensional silhouettes of the model to edge-detected versions of the X-ray images to produce an accuracy score, as described with reference to FIGS. 3-7 (e.g., importing the models into a workspace, reconstructing the locations of the X-ray sources, raytracing from the locations of the X-ray sources to produce three-dimensional silhouettes, producing two-dimensional silhouettes from projections of the three-dimensional silhouettes, applying edge detection to the two-dimensional X-ray images from the image production device 112 to produce edge-detected versions of the X-ray images, comparing the two-dimensional silhouettes to the edge-detected versions of the X-ray images). Any differences (e.g., non-overlapping lines) between the two-dimensional silhouettes and the corresponding edge-detected versions of the X-ray images reduce the accuracy score, while similarities (e.g. overlapping lines) increase the accuracy score. For purposes of the example, the accuracy score may be 7.

The model production device 110 then repeats the process of obtaining a candidate model, this time using different translation and rotation values. For example, translation values of x=30, y=30, z=30 and rotation values of x=30, y=30, z=30 are used. The resulting accuracy score is 8. Subsequently, the model production device repeats the process with translation values of x=40, y=40, z=40 and the accuracy score drops to 6. Based on the drop in the accuracy score, the model production device 110 tests various values within the range of 20 to 30 for translation and rotation, until the model production device 110 determines that the highest score of 9 was reached with translation values of x=28, y=28, z=28 and rotation values of x=24, y=20, z=26. Subsequently, the model production device 110 indicates to a user or other device that the model produced using the translation values of x=28, y=28, z=28 and rotation values of x=24, y=20, z=26 is the most accurate model of the bone(s) in the knee joint.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A device comprising:
   circuitry to:
   obtain two-dimensional images of a bone of a knee joint;
   obtain a candidate three-dimensional model of the bone from the two-dimensional images;
   produce two-dimensional silhouettes of the candidate three-dimensional model;
   apply an edge detection algorithm to the two-dimensional images to produce corresponding edge images; and
   compare the two-dimensional silhouettes to the edge images to produce a score indicative of an accuracy of the candidate three-dimensional model.

2. The device of claim 1, wherein the circuitry is to obtain the candidate three-dimensional model of the bone using the two-dimensional images and reference models of bones of human knee joints.

3. The device of claim 1, wherein the bone is a femur, and wherein at least one condylar profile is visible in the two-dimensional silhouettes and the edge images.

4. The device of claim 3, wherein the at least one condylar profile is a sagittal condylar profile.

5. The device of claim 3, wherein an intercondylar notch of the femur is visible in the two-dimensional silhouettes and the edge images.

6. The device of claim 5, wherein medial and lateral epicondyles of the femur are visible in the two-dimensional silhouettes and the edge images.

7. The device of claim 1, wherein the bone is a tibia, and wherein at least one condylar profile is visible in the two-dimensional silhouettes and the edge images.

8. The device of claim 7, wherein the at least one condylar profile is a sagittal condylar profile.

9. The device of claim 7, wherein an intercondylar eminence of the tibia is visible in the two-dimensional silhouettes and the edge images.

10. The device of claim 1, wherein the circuitry is further to:
    position the two-dimensional images and the candidate three-dimensional model in a three-dimensional space; and
    determine positions in three dimensions of x-ray sources utilized to produce the two-dimensional images.

11. The device of claim 10, wherein the circuitry is further to trace rays from a determined position of an x-ray source utilized to produce one of the two-dimensional images to the corresponding two-dimensional image.

12. The device of claim 11, wherein the circuitry is further to identify, for each ray, polygons on a surface of the candidate three-dimensional model that intersect the ray.

13. The device of claim 12, wherein the polygons identified for each ray are adjacent and arranged in opposing orientations.

14. The device of claim 13, wherein the circuitry is further to determine one or more common edges between the polygons identified for each ray.

15. The device of claim 1, wherein the circuitry is further to apply a mask to the two-dimensional images to remove an object from the two-dimensional images.

16. The device of claim 1, wherein to compare the two-dimensional silhouettes to the edge images to produce a score indicative of an accuracy of the candidate three-dimensional model comprises to:
    locate, in the edge images, pixel values that correspond to edges in the two-dimensional silhouettes; and
    sum the located pixel values.

17. One or more non-transitory machine-readable storage media comprising a plurality of instructions stored thereon that, in response to being executed, cause a device to:
    obtain two-dimensional images of a bone of a knee joint;
    obtain a candidate three-dimensional model of the bone from the two-dimensional images;
    produce two-dimensional silhouettes of the candidate three-dimensional model;
    apply an edge detection algorithm to the two-dimensional images to produce corresponding edge images; and
    compare the two-dimensional silhouettes to the edge images to produce a score indicative of an accuracy of the candidate three-dimensional model.

18. The one or more non-transitory machine-readable storage media of claim 17, wherein the plurality of instructions cause the device to obtain the candidate three-dimensional model of the bone using the two-dimensional images and reference models of bones of human knee joints.

19. A method comprising:
    obtaining, by a device, two-dimensional images of a bone of a knee joint;
    obtaining, by the device, a candidate three-dimensional model of the bone from the two-dimensional images;
    producing, by the device, two-dimensional silhouettes of the candidate three-dimensional model;

applying, by the device, an edge detection algorithm to the two-dimensional images to produce corresponding edge images; and comparing, by the device, the two-dimensional silhouettes to the edge images to produce a score indicative of an accuracy of the candidate three-dimensional model.

20. The method of claim 19, wherein obtaining the candidate three-dimensional model of the bone comprises obtaining the candidate three-dimensional model of the bone using the two-dimensional images and reference models of bones of human knee joints.

* * * * *